United States Patent
Mikami

(10) Patent No.: US 8,275,447 B2
(45) Date of Patent: Sep. 25, 2012

(54) MEDICAL IMAGE DIAGNOSTIC SYSTEM, MEDICAL IMAGING APPARATUS, MEDICAL IMAGE STORAGE APPARATUS, AND MEDICAL IMAGE DISPLAY APPARATUS

(75) Inventor: Yuji Mikami, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1035 days.

(21) Appl. No.: 12/237,708

(22) Filed: Sep. 25, 2008

(65) Prior Publication Data
US 2009/0088637 A1    Apr. 2, 2009

(30) Foreign Application Priority Data
Sep. 28, 2007   (JP) .................................. 2007-255574

(51) Int. Cl.
*A61B 5/05*    (2006.01)
(52) U.S. Cl. ........ 600/427; 600/407; 600/437; 600/443; 600/447
(58) Field of Classification Search ................... 600/407, 600/437, 443, 447
See application file for complete search history.

(56) References Cited

U.S. PATENT DOCUMENTS
7,556,602 B2 * 7/2009 Wang et al. .................... 600/437
2010/0022881 A1 * 1/2010 Fujita et al. .................... 600/445

FOREIGN PATENT DOCUMENTS
JP    2005-312770 A    11/2005

\* cited by examiner

*Primary Examiner* — Brian Casler
*Assistant Examiner* — Joel Lamprecht
(74) *Attorney, Agent, or Firm* — Sughrue Mion, PLLC

(57) ABSTRACT

In a system for diagnoses of mammary glands and breasts using radiation and ultrasonic waves in combination, images are correlated for easier visual recognition. The system includes an apparatus for acquiring a radiation image of an object projected on a projection surface, acquiring an ultrasonic slice image of the object along a slice surface substantially orthogonal to the projection surface, and generating first image data representing ultrasonic slice images along slice surfaces, second image data representing a radiation image, and location data representing locations of the slice surfaces on the projection surface; an apparatus for correlating and storing those data; and an apparatus for displaying an ultrasonic slice image based on the first image data, and displaying a radiation image, on which a marker indicating a location of the slice surface on the projection surface is shown, based on the second data and the location data.

18 Claims, 7 Drawing Sheets

MEDICAL IMAGE DIAGNOSTIC SYSTEM, MEDICAL IMAGING APPARATUS, MEDICAL IMAGE STORAGE APPARATUS, AND MEDICAL IMAGE DISPLAY APPARATUS

BACKGROUND OF THE INVENTION

1. Field of the Invention

The present invention relates to a medical image diagnostic system to be used for diagnoses of breast cancer or the like by imaging mammary glands and breasts by using radiation and ultrasonic waves in combination. Further, the present invention relates to a medical imaging apparatus, a medical image storage apparatus, and a medical image display apparatus to be used in the medical image diagnostic system.

2. Description of a Related Art

Conventionally, an imaging method using radiation (X-ray, $\alpha$-ray, $\beta$-ray, $\gamma$-ray, electron ray, ultraviolet ray, or the like) is utilized in various fields, and particularly, in the medical field, the method is one of the most important means for diagnoses. Radiation images obtained by X-ray imaging (X-ray mammography) of mammary glands and breasts for breast cancer diagnoses are useful for finding calcification as a precursor, but finding calcification may be difficult depending on the age of a subject. Accordingly, it has been studied to use radiation and ultrasonic wave in combination to make diagnoses based on both radiation images and ultrasonic images. X-ray mammography and ultrasonic imaging have the following features, respectively.

X-ray mammography is suitable for exposing calcification as one of early symptoms of a cancer, and enables detection with high sensitivity and high resolving power. Especially, in the case where mammary gland tissues have become atrophied and replaced with fat (so-called "fat breast") as is the case of postmenopausal women, more information can be obtained by X-ray mammography. However, the X-ray imaging has a disadvantage that detection capability of specific natures of tissues (tissue properties) is low.

Further, in an X-ray image, mammary glands are expressed in homogeneous soft tissue density, and thus, the detection of tumor mass is difficult for the case where mammary glands have developed (so-called, "dense breast") as is the case of adolescent to premenopausal women. Furthermore, in X-ray mammography, only two-dimensional images can be obtained in which an object to be inspected as a solid is projected on a plane. On this account, even when a tumor mass is found, it is difficult to grasp information on the locations in the depth direction, size, and so on of the tumor mass.

On the other hand, in ultrasonic imaging, specific natures of tissues (e.g., the difference between a cystic tumor and a solid matter) can be detected, and also, a lobular cancer can be detected. Further, real time observation of images and three-dimensional image generation are possible. However, ultrasonic imaging examination often depends on the skill of an operator such as a doctor in accuracy and provides low reproducibility. Further, it is difficult to observe minute calcification in an ultrasonic image.

As described above, X-ray mammography examination and ultrasonic imaging examination have both merits and demerits, and it is desirable that both examinations are performed for reliably finding breast cancer.

As a related technology, Japanese Patent Application Publication JP-P2005-312770A discloses an ultrasonic diagnostic apparatus capable of displaying ultrasonic images for observation within a body of an object to be inspected with guide images anatomically and precisely corresponding to the ultrasonic images. The ultrasonic diagnostic apparatus includes image processing control means for generating guide images corresponding to anatomic location and orientation of two-dimensional ultrasonic images based on anatomic image data stored as anatomic image data of a human body in advance, and display means for displaying a plurality of various images including the guide images and two-dimensional ultrasonic images. However, JP-P2005-312770A does not disclose that plural images obtained by respectively using plural different imaging modalities are correlated and displayed.

SUMMARY OF THE INVENTION

The present invention has been achieved in view of the above-mentioned problems. A purpose of the present invention is, in a medical image diagnostic system to be used for diagnoses of breast cancer or the like by imaging mammary glands and breasts by using radiation and ultrasonic waves in combination, to correlate radiation images and ultrasonic images for easier visual recognition.

In order to accomplish the above-mentioned purpose, a medical image diagnostic system according to one aspect of the present invention includes a medical imaging apparatus for acquiring a radiation image of an object to be inspected projected on a projection surface by applying radiation to the object, acquiring an ultrasonic slice image of the object along a slice surface substantially orthogonal to the projection surface by transmitting ultrasonic waves toward the object and receiving ultrasonic echoes reflected by the object, and generating first image data representing plural ultrasonic slice images along plural slice surfaces, second image data representing at least one radiation image, and location data representing locations of the plural slice surfaces on the projection surface; a medical image storage apparatus for correlating and storing the first image data, the second image data, and the location data generated by the medical imaging apparatus; and a medical image display apparatus for displaying at least one ultrasonic slice image along at least one slice surface based on the first image data loaded from the medical image storage apparatus, and displaying at least one radiation image, on which a marker indicating a location of the at least one slice surface on the projection surface is shown, based on the second image data and the location data loaded from the medical image storage apparatus.

According to the present invention, the ultrasonic slice image along the slice surface substantially perpendicular to the projection surface of the radiation image is displayed and the radiation image, on which the location of the slice surface on the projection surface is indicated, is displayed, and therefore, the radiation image and the ultrasonic image are correlated for easier visual recognition. Thereby, detection capabilities of two different imaging modalities can be mutually complemented, and easier grasping of spatial locations and higher detection capability of diseased issues can be realized.

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted.

Figure 1:
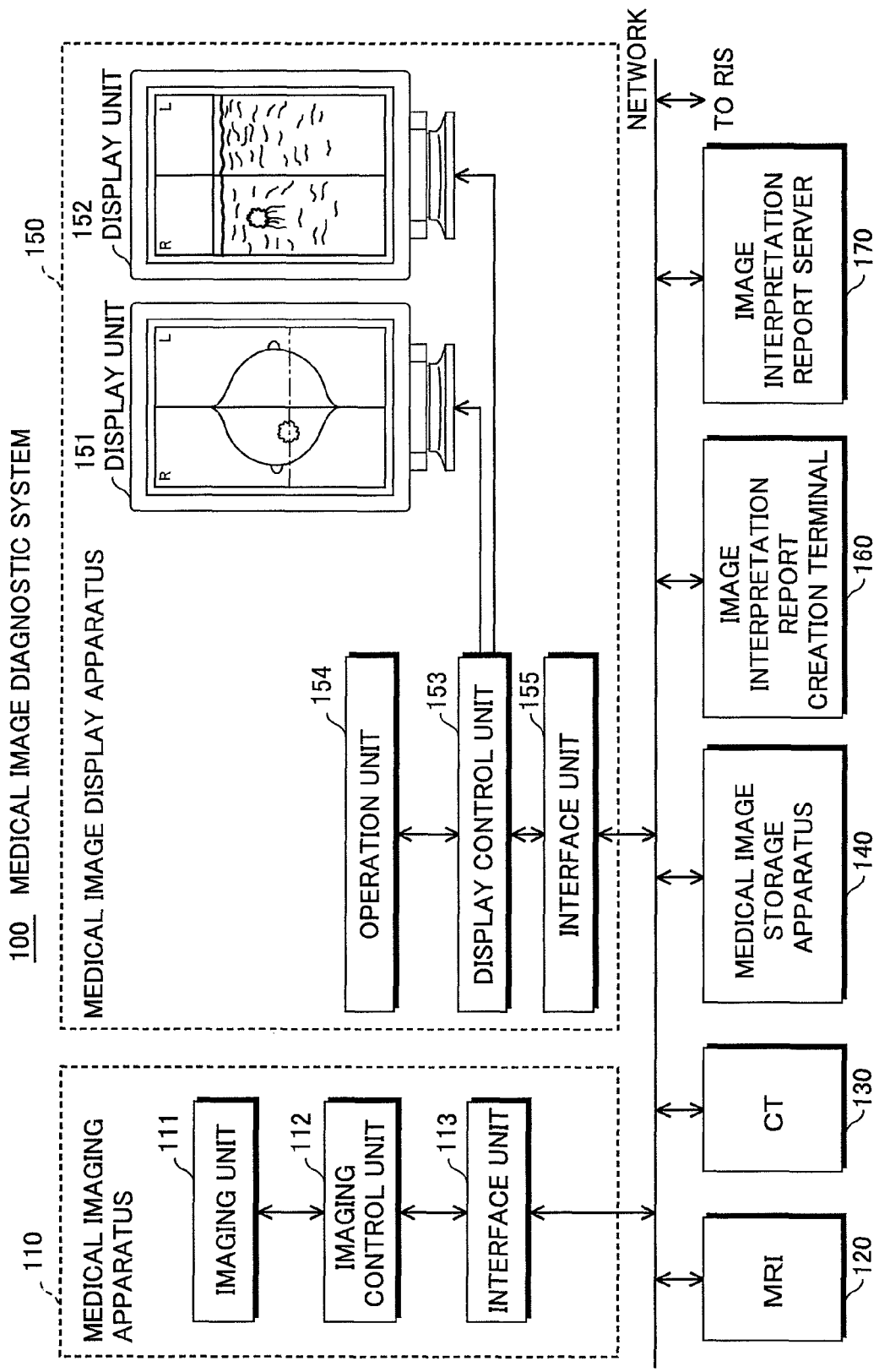
FIG. 1 is a block diagram showing a configuration of a medical image diagnostic system according to one embodiment of the present invention.

FIG. 1 is a block diagram showing a configuration of a medical image diagnostic system according to one embodiment of the present invention. As shown in FIG. 1, the medical image diagnostic system 100 includes a medical imaging apparatus 110, a medical image storage apparatus 140, and a medical image display apparatus 150. Further, the medical image diagnostic system 100 may include imaging modalities such as an MRI apparatus 120 and a CT apparatus 130, an image interpretation report creation terminal 160, and an image interpretation report server 170. These apparatuses are connected to one another via a network such as LAN (local area network). Furthermore, the medical image diagnostic system 100 may be connected to an RIS (radiology information system).

The medical imaging apparatus 110 has an imaging unit 111 for performing radiation imaging and ultrasonic imaging, an imaging control section 112 for controlling imaging operation in the imaging unit 111, and an interface unit 113 for communication between the medical image storage apparatus 140 and so on and itself via the network.

The medical image storage apparatus 140 is a server for PACS (Picture Archiving and Communication System) for storage and management of image data acquired by various imaging modalities such as the medical imaging apparatus 110, MR apparatus 120, and CT apparatus.

The medical image display apparatus 150 has display units 151 and 152 as high-definition displays (viewers), a display control unit 153 for controlling image display operation in the display units 151 and 152, an operation unit 154 for an operator to operate for selection of image display contents, and an interface unit 155 for communication between the medical image storage apparatus 140 and so on and itself via the network.

The image interpretation report creation terminal 160 is an apparatus for an image interpretation doctor to use for creating image interpretation reports while viewing the medical images displayed on the medical image display apparatus 150. The report data representing the image interpretation reports created by the image interpretation doctor is stored in the image interpretation report server 170.

Figure 2:
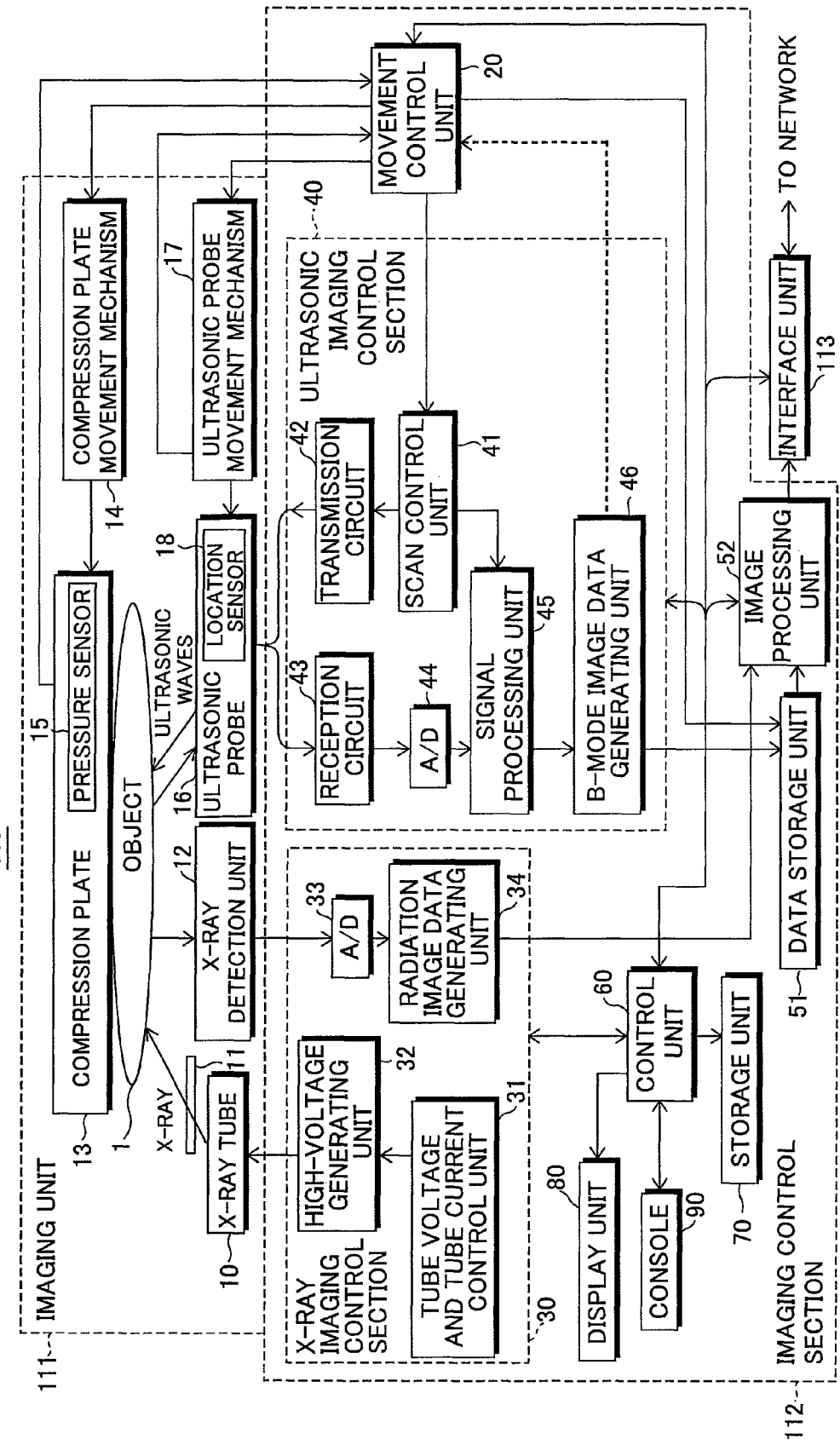
FIG. 2 is a block diagram showing a detailed configuration of a medical imaging apparatus according to one embodiment of the present invention.

FIG. 2 is a block diagram showing a detailed configuration of a medical imaging apparatus according to one embodiment of the present invention. The medical imaging apparatus has both a function of a radiation mammography apparatus for applying radiation to a breast, detecting the radiation transmitted through the breast, and thereby, generating a radiation image, and a function of an ultrasonic diagnostic apparatus for transmitting ultrasonic waves to the breast, receiving ultrasonic echoes reflected within the breast, and thereby, generating ultrasonic images. As below, the case of using an X-ray as radiation will be explained, however, α-ray, β-ray, γ-ray, electron ray, ultraviolet ray, or the like may be used.

As shown in FIG. 2, the imaging unit 111 has an X-ray tube 10, a filter 11, an X-ray detection unit 12 for detecting an X-ray generated by the X-ray tube 10 and transmitted through an object to be inspected 1, a compression plate 13 for pressing a breast as the object, a compression plate movement mechanism 14 for moving the compression plate 13, a pressure sensor 15 for detecting pressure applied to the compression plate 13, an ultrasonic probe 16 including plural ultrasonic transducers for transmitting and receiving ultrasonic waves, an ultrasonic probe movement mechanism 17 for moving the ultrasonic probe 16, and a location sensor 18 for detecting location of the ultrasonic probe 16.

Figure 3:
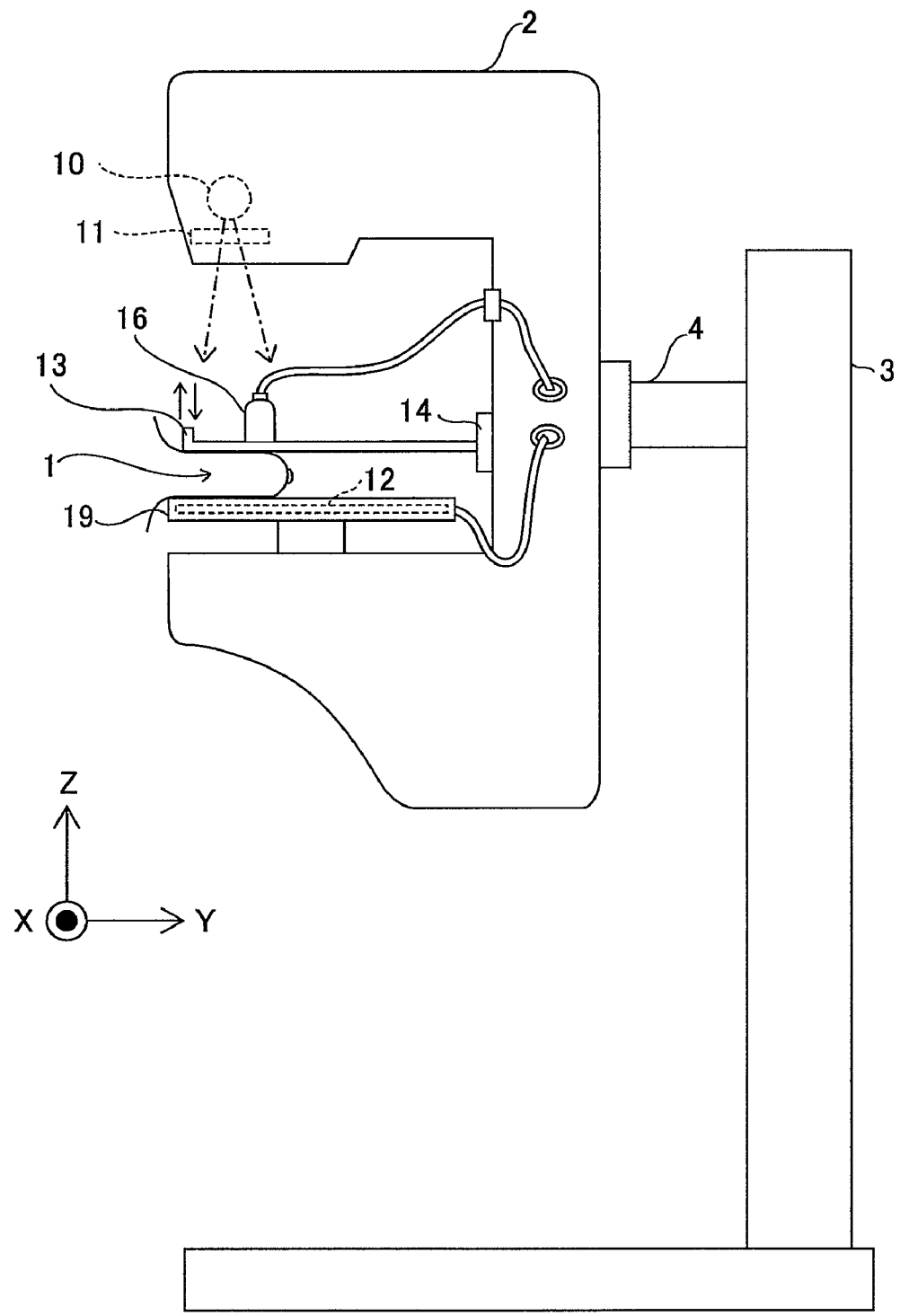
FIG. 3 is a side view showing an appearance of an imaging unit of the medical imaging apparatus shown in FIG. 2.

FIG. 3 is a side view showing an appearance of the imaging unit of the medical imaging apparatus shown in FIG. 2. As shown in FIG. 3, the imaging unit 111 has an arm part 2, a support 3 for movably holding the arm part 2 in the vertical direction (Z-axis direction), and a shaft part 4 for connecting the arm 2 to the support 3. The arm part 2 is provided with the X-ray tube 10, the filter unit 11, the X-ray detection unit 12, an imaging stage 19 located between the X-ray tube 10 and the X-ray detection unit 12, the compression plate 13 for pressing the object 1 between the imaging stage 19 and itself, the compression plate movement mechanism 14 for moving the compression plate 13 in the vertical direction (Z-axis direction), and the ultrasonic probe 16.

The X-ray tube 10 and the filter 11 form a radiation emitting section. The X-ray tube 10 emits an X-ray when a tube voltage is applied thereto. The filter 11 is made of a material such as molybdenum (Mo) or rhodium (Rh), and selectively transmits a desired wavelength component of plural wavelength components contained in the X-ray emitted by the X-ray tube 10. The X-ray detection unit 12 is a flat panel X-ray detector (FPD) for imaging an X-ray image by detecting the X-ray transmitted through the object 1 at plural detection points in a two-dimensional region. The X-ray radiated from the X-ray tube 10 and transmitted through the object 1 is applied to the respective detection points, and thereby, detection signals having magnitudes corresponding to the intensity of the X-ray are outputted from the X-ray detection unit 12. The detection signals are inputted via a cable to an X-ray imaging control section 30 (FIG. 2).

The compression plate 13 is provided in parallel to the imaging stage 19, and the compression plate movement mechanism 14 moves the compression plate 13 in the Z-axis direction. The pressure sensor 15 detects the pressure applied to the compression plate 13 and a movement control unit 20 (FIG. 2) controls the compression plate movement mechanism 14 based on the detection result. The object (breast) 1 is sandwiched by the compression plate 13 and the imaging stage 19, and X-ray imaging is performed with the homogeneous thickness of the breast. Thereby, a radiation image of the breast projected on the projection surface (the detection surface of the X-ray detection unit 12) is acquired. X-ray imaging is performed at least once for each of the right and left breasts.

Here, the compression plate 13 is necessary to be optically transparent for positioning when the breast is compressed or confirmation of the compression state, and desirably formed of a material that transmits the X-ray radiated from the X-ray tube 10 and easily propagates ultrasonic waves to be transmitted from the ultrasonic probe 16. As a material of the compression plate 13, a resin such as polymethylpentene having suitable values in acoustic impedance that affects the reflectance of ultrasonic waves and attenuation coefficient that affects the attenuation of ultrasonic waves may be used, for example.

The ultrasonic probe 16 includes one-dimensionally or two-dimensionally arranged plural ultrasonic transducers. Each ultrasonic transducer transmits ultrasonic waves to the object based on the applied drive signal, and receives ultrasonic echoes reflected from the object and outputs a reception signal.

Each ultrasonic transducer is configured by a vibrator in which electrodes are formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a voltage is applied to the electrodes of the vibrator by transmitting pulsed or continuous wave electric signals, the piezoelectric material expands and contracts. By the expansion and contraction, pulsed or continuous wave ultrasonic waves are generated from the respective vibrators, and an ultrasonic beam is formed by synthesizing these ultrasonic waves. Further, the respective vibrators expand and contract by receiving propagating ultrasonic waves and generate electric signals. These electric signals are outputted as reception signals of the ultrasonic waves, and inputted to the ultrasonic imaging control section 40 (FIG. 2) via a cable.

The ultrasonic probe 16 may be moved in close contact with the compression plate 13, or, after insertion of an ultrasonic transmission medium such as echo gel between the compression plate 13 and itself, may be moved apart from the compression plate 13. In either case, the ultrasonic probe 16 moves along an opposite surface to the pressure surface of the compression plate 13 while keeping acoustic connection (coupling) between the surface and itself. Further, the operator may move the ultrasonic probe 16, or the ultrasonic probe movement mechanism 17 shown in FIG. 2 may move the ultrasonic probe 16. As below, the latter case will be explained.

Referring to FIG. 2 again, the imaging control section 112 has the movement control unit 20 for controlling the compression plate movement mechanism 14, the ultrasonic probe movement mechanism 17, and so on, the X-ray imaging control section 30, the ultrasonic imaging control section 40, a data storage unit 51, an image processing unit 52, a control unit 60, a storage unit 70, a display unit 80, and a console 90.

The location of the ultrasonic probe 16 is detected by the location sensor 18 provided in the ultrasonic probe 16. The movement control unit 20 grasps the location of the ultrasonic probe 16 based on the output signal of the location sensor 18 and controls the ultrasonic probe movement mechanism 17. Alternatively, plural location indicators that readily reflect ultrasonic waves are provided on the compression plate 13 or imaging stage 19, and the movement control unit 20 may grasp the location of the ultrasonic probe 16 based on the contents of ultrasonic slice images represented by B-mode image data sequentially generated by a B-mode image data generating unit 46. The movement control unit 20 generates location data representing a location of a slice surface (slice location) of an ultrasonic slice image. The location data represents an X-coordinate of the ultrasonic probe 16 at radiation imaging, for example, and is correlated to an X-coordinate in the radiation image.

The X-ray imaging control section 30 includes a tube voltage and tube current control unit 31, a high-voltage generating unit 32, an A/D converter 33, and a radiation image data generating unit 34. In the X-ray tube 10, the X-ray transparency is determined according to the tube voltage applied between the cathode and the anode, and the amount of X-ray emission is determined according to the time integration of the tube current flowing between the cathode and the anode. The tube voltage and tube current control unit 31 adjusts imaging conditions of the tube voltage, tube current, and so on according to target values. The target values of the tube voltage and the tube current may be manually adjusted by the operator using the console 90. The high-voltage generating unit 32 generates a high voltage to be applied to the X-ray tube 10 under the control of the tube voltage and tube current control unit 31. The A/D converter 33 converts analog radiation detection signals outputted from the X-ray detection unit 12 into digital signals (radiation detection data), and the radiation image data generating unit 34 generates radiation image data based on the radiation detection data.

The ultrasonic imaging control section 40 includes a scan control unit 41, a transmission circuit 42, a reception circuit 43, an A/D converter 44, a signal processing unit 45, and a B-mode image data generating unit 46. The scan control unit 41 sets frequencies and voltages of the drive signals to be applied from the transmission circuit 42 to the respective ultrasonic transducers of the ultrasonic probe 16 and adjusts the frequency and sound pressure of the ultrasonic waves to be transmitted under the control of the movement control unit 20. Further, the scan control unit 41 has a transmission control function of transmission directions of ultrasonic beams and selecting transmission delay patterns according to the set transmission directions, and a reception control function of sequentially setting reception directions of ultrasonic echoes and selecting reception delay patterns according to the set reception directions.

Here, the transmission delay pattern refers to a delay time pattern to be provided to the plural drive signals for forming an ultrasonic beam in a desired direction with the ultrasonic waves transmitted from the plural ultrasonic transducers of the ultrasonic probe 16, and the reception delay pattern refers to a delay time pattern to be provided to the plural reception signals for extracting ultrasonic echoes from the desired direction with the ultrasonic waves received by the plural ultrasonic transducers. Plural transmission delay patterns and reception delay patterns are stored in a memory or the like.

The transmission circuit 42 generates plural drive signals to be respectively applied to the plural ultrasonic transducers. In this regard, the transmission circuit 42 may adjust the amounts of delay of the plural drive signals and supply the signals to the ultrasonic probe 16 so that the ultrasonic waves to be transmitted from the plural ultrasonic transducers form an ultrasonic beam, or may supply plural drive signals to the ultrasonic probe 16 so that the ultrasonic waves to be transmitted at once from the plural ultrasonic transducers reach the entire imaging region of the object.

The reception circuit 43 amplifies the plural ultrasonic reception signals respectively outputted from the plural ultrasonic transducers, and the A/D converter 44 converts the analog ultrasonic reception signals amplified by the reception circuit 43 into digital ultrasonic reception signals. The signal processing unit 45 performs reception focus processing by providing the respective delay times to the plural ultrasonic reception signals based on the reception delay pattern selected by the scan control unit 41, and adding those ultrasonic reception signals. Through the reception focus processing, sound ray data in which the focal point of the ultrasonic echoes is narrowed is formed.

Furthermore, the signal processing unit 45 corrects attenuation of the sound ray data by distance according to the depths of the reflection positions of ultrasonic waves through STC (Sensitivity Time gain Control), and then, performs envelope detection processing with a low-pass filter or the like thereon to generate envelope data.

The B-mode image data generating unit 46 performs processing such as logarithmic compression and gain adjustment on the envelope data to generate image data, and converts (raster-converts) the image data into image data that follows the normal scan system of television signals to generate B-mode image data.

The data storage unit 51 is configured by a hard disk, memory, or the like, and stores the B-mode image data generated by the B-mode image data generating unit 46. In this regard, the ultrasonic slice images along the respective slice surface are correlated to location data representing the locations of the slice surfaces (slice locations) and stored.

The image processing unit 52 performs necessary image processing such as gradation processing on the B-mode data loaded from the data storage unit 51 to generate first image data for display, and performs necessary image processing such as gradation processing on the radiation image data outputted from the radiation image data generating unit 34 to generate second image data for display. Alternatively, the image processing unit 52 may generate first image data representing ultrasonic images of the right and left breasts within one screen and second image data representing radiation images of the right and left breasts within one screen for comparison and observation of the images of the right and left breasts. The image processing unit 52 outputs the first and second image data to the interface unit 113 together with the ultrasonic slice image location data.

The control unit 60 controls the respective parts based on the operation of the operator. The display unit 80 is configured by an LCD display or the like, and used for image confirmation at imaging and display of an operation screen or the like. The console 90 is used by the operator to operate the medical imaging apparatus. So far, the movement control unit 20, the radiation image data generating unit 34, the scan control unit 41, the signal processing unit 45, the B-mode image data generating unit 46, the image processing unit 52, and the control unit 60 are configured by a central processing unit (CPU) and software for allowing the CPU to execute various kinds of processing, however, they may be configured by a digital circuit or analog circuit. The software (program) is stored in the storage unit 70 formed by a hard disk, memory, or the like. Further, the transmission delay patterns and the reception delay patterns to be selected by the scan control unit 41 may be stored in the storage unit 70.

The interface unit 113 transmits the first and second image data and the location data outputted from the image processing unit 52 as data files via the network to the medical image storage apparatus 140 (FIG. 1).

Figure 4:
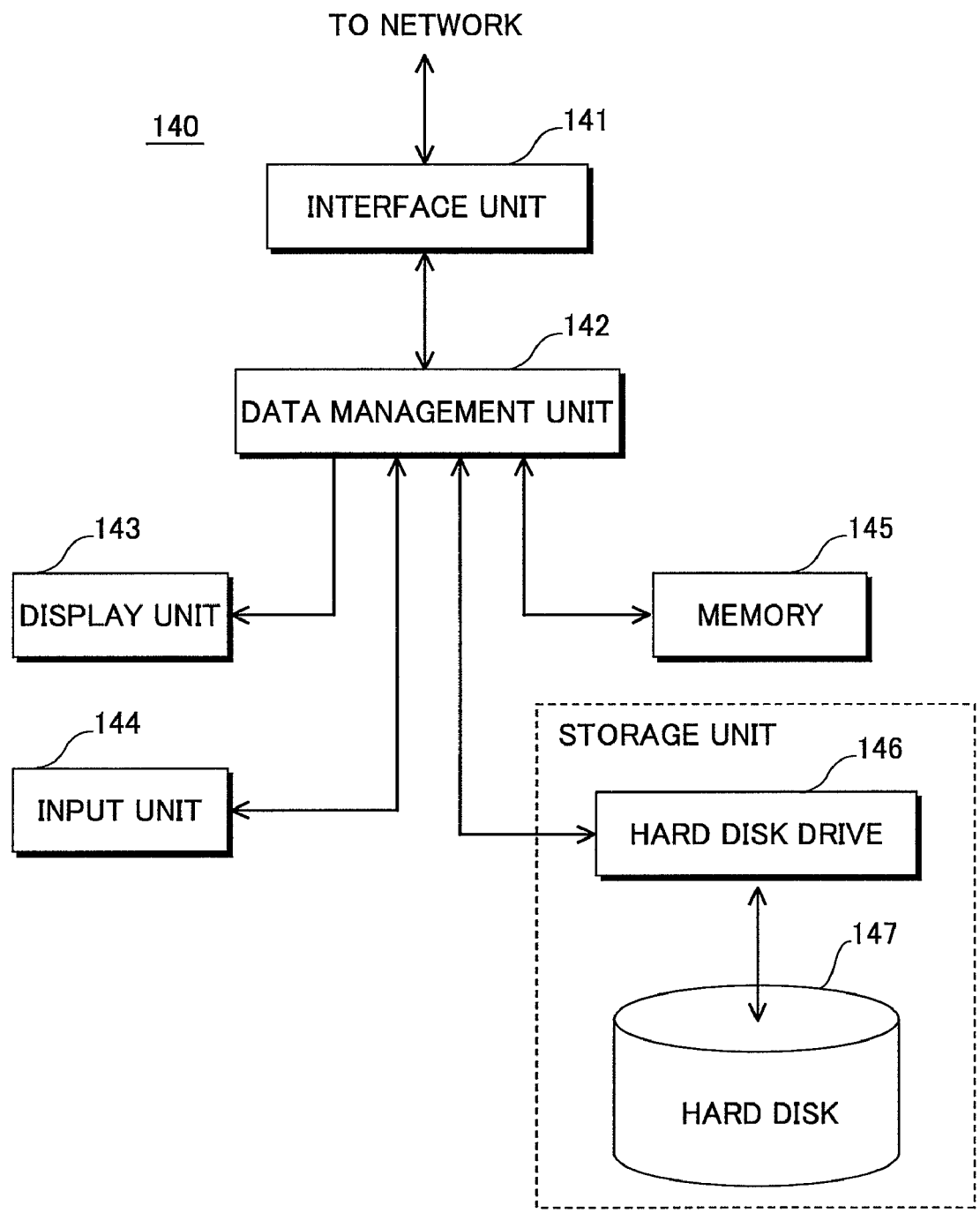
FIG. 4 is a block diagram showing a configuration of a medical image storage apparatus according to one embodiment of the present invention.

FIG. 4 is a block diagram showing a configuration of a medical image storage apparatus according to one embodiment of the present invention. The medical image storage apparatus 140 includes an interface unit 141 for communication between the various imaging modalities, medical image display apparatus, and so on and itself via the network, a data management unit 142 for management of image data and so on transmitted from the medical imaging apparatus 110 (FIG. 1) and other imaging modalities, a display unit 143 as an LCD display or the like for displaying an operation screen and so on, an input unit 144 including a keyboard and a mouse used for inputting various commands and so on, a memory 145 for temporarily storing image data and so on, and a hard disk drive 146 and a hard disk 147 forming a storage unit. The hard disk 147 is a recording medium for storing image data and so on as data files. The hard disk drive 146 records and reproduces the image data and so on in the hard disk 147 under the management of the data management unit 142.

The interface unit 141 receives the first and second image data and the local data obtained by the medical imaging apparatus 110 via the network from the medical imaging apparatus 110 (FIG. 1). The data management unit 142 correlates the first image data representing plural ultrasonic slice images along plural slice surfaces, the second image data representing at least one radiation image, and the location data representing locations of the plural slice surfaces on the projection surface to one another based on those data, and allows the storage unit to store the data.

The data management unit 142 is configured by a central processing unit (CPU) and software for allowing the CPU to execute various kinds of processing, however, the data management unit 142 may be configured by a digital circuit or analog circuit. The software (program) is stored in the storage unit.

The medical image display apparatus 150 shown in FIG. 1 loads the first and second image data and the location data stored in the medical image storage apparatus 140, displays at least one ultrasonic slice image along at least one slice surface based on the first image data, and displays at least one radiation image including a marker indicating the at least one slice surface in the projection surface based on the second image data and the location data.

For example, the display control unit 153 of the medical image display apparatus outputs the first image data to the display unit 152 and outputs the second image data and the location data to the display unit 151. Thereby, the ultrasonic image is displayed on the display unit 152, and the radiation image and the marker are displayed on the display unit 151. Alternatively, the ultrasonic image, the radiation image, or a synthesized image may be displayed on one display unit.

The image processing unit 52 of the medical imaging apparatus shown in FIG. 2 performs rotation processing and flip (vertical flip) processing of images, and thereby, regarding symmetric organs of the object, generates first image signals representing an ultrasonic slice image of a left tissue along the first slice surface and an ultrasonic slice image of a right tissue along the second slice surface symmetrically with a line segment at a predetermined distance within the object as a central axis. Further, the image processing unit 52 generates second image signals representing a radiation image of the left tissue in which the location of the first slice surface on the projection surface is indicated and a radiation image of the right tissue in which the location of the second slice surface on the projection surface is indicated symmetrically with a line segment at a predetermined distance within the object as a central axis.

Figure 5:
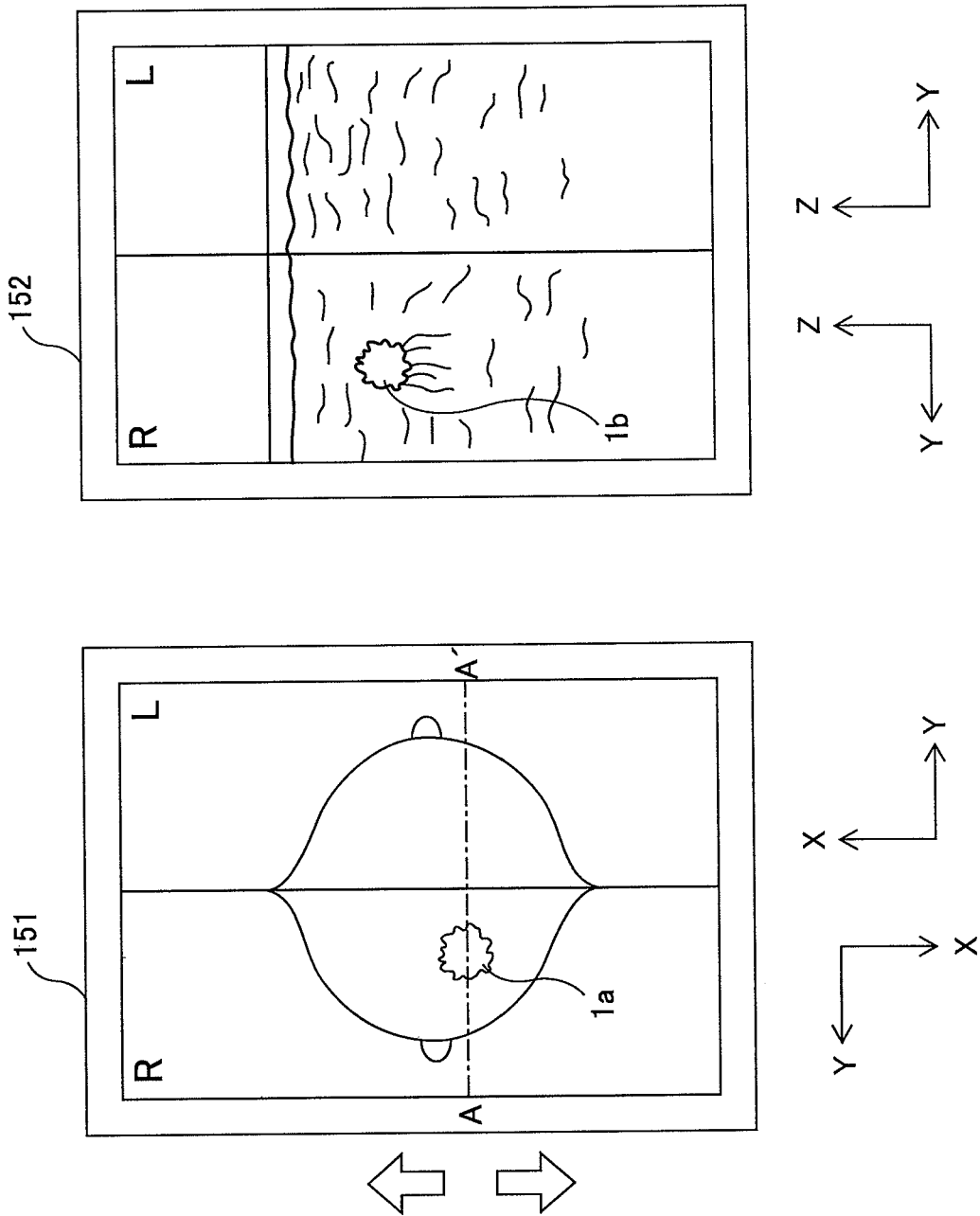
FIG. 5 shows an example of radiation images and ultrasonic images displayed on the display unit.

FIG. 5 shows an example of radiation images and ultrasonic images displayed on the display unit. In this example, ultrasonic images representing right and left breasts are displayed on the display unit 152, and radiation images representing the right and left breasts and a marker are displayed on the display unit 151.

The image processing unit 52 (FIG. 2) generates first image signals representing an ultrasonic slice image of a left breast (L) along the first slice surface and an ultrasonic slice image of a right breast (R) along the second slice surface symmetrically with respect to the Y-axis direction with a line of the chest wall as a central axis. Further, the image processing unit 52 generates second image signals representing a radiation image of the left breast (L) in which the location of the first slice surface on the projection surface is indicated and a radiation image of the right breast (R) in which the location of the second slice surface on the projection surface is indicated symmetrically with respect to the X-axis direction and the Y-axis direction with a line of the chest wall as a central axis.

As shown in FIG. 5, in the radiation image displayed on the display unit 151, the location of the slice surface of the ultrasonic slice image is indicated by the marker (a dashed-dotted line A-A'). An operator is able to move the locations of the markers indicated in the radiation images with respect to the right and left breast together or independently in the vertical direction by operating the operation unit 154 shown in FIG. 1.

When the operator moves the location of the marker, the display control unit 153 allows the display unit 152 to display an ultrasonic slice image along a slice surface corresponding to the location designated by the marker based on the first image data stored in the medical image storage apparatus 140. Thereby, the operator is able to observe a region 1b of the ultrasonic image corresponding to a region 1a of interest in the radiation image.

Alternatively, the operator is able to change the ultrasonic images displayed on the display unit 152 with respect to the right and left breast together or independently by operating the operation unit 154 shown in FIG. 1. When the operator changes the ultrasonic image, the display control unit 153 changes the location of the marker displayed on the display unit 151 to indicate the location of a slice surface of a new ultrasonic slice image. Thereby, the operator is able to observe the region 1a of the radiation image corresponding to the region 1b of interest in the ultrasonic image.

Figure 6:
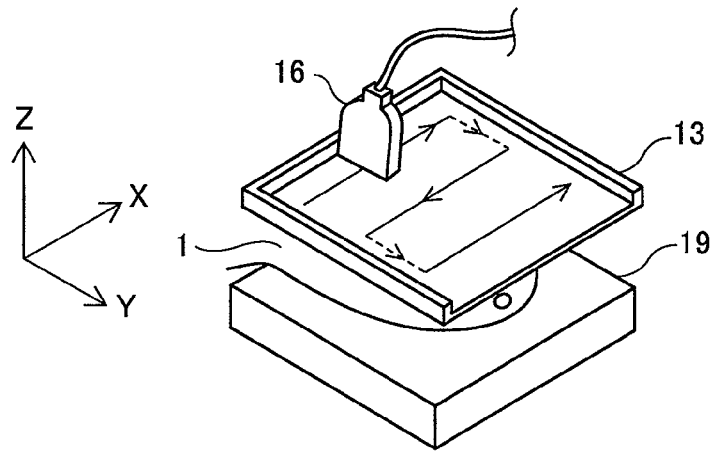
FIG. 6 shows a first example of a procedure of scanning the object by moving an ultrasonic probe.
Figure 7:
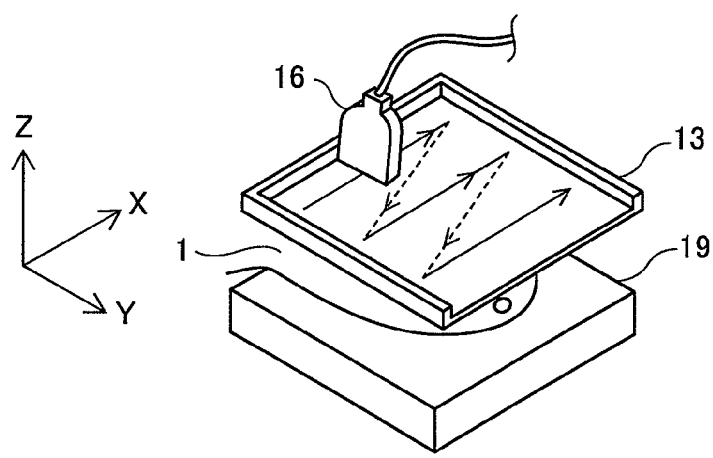
FIG. 7 shows a second example of the procedure of scanning the object by moving the ultrasonic probe.
Figure 8:
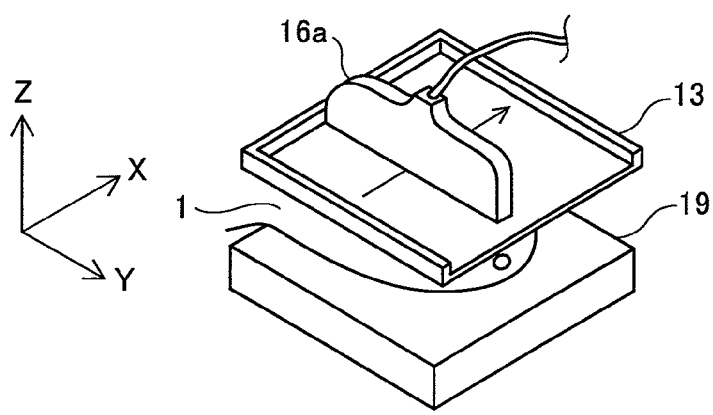
FIG. 8 shows a third example of the procedure of scanning the object by moving the ultrasonic probe.

FIGS. 6-8 show first to third examples of a procedure of scanning the object by moving the ultrasonic probe. The object (breast) 1 is sandwiched between the compression plate 13 and the imaging stage 19, and the movement control unit 20 controls the ultrasonic probe movement mechanism 17 and the scan control unit 41 so that the ultrasonic probe 16 transmits and receives ultrasonic waves while the ultrasonic probe movement mechanism 17 moves the ultrasonic probe 16. Thereby, the B-mode image data representing plural ultrasonic slice images of the object 1 along the plural slice surfaces are sequentially generated. Typically, the ultrasonic imaging is performed at least once for the respective right and left breasts. In FIGS. 6-8, since the ultrasonic probe 16 is substantially orthogonal to the compression plate 13 and the imaging stage 19, the respective slice surfaces are substantially orthogonal to the projection surface of X-ray image.

In the first example shown in FIG. 6, the ultrasonic probe 16 first performs the first scan by transmitting and receiving ultrasonic waves while moving in the positive X-axis direction, then, moves to a predetermined distance in the positive Y-axis direction, and performs the second scan by transmitting and receiving ultrasonic waves while moving in the negative X-axis direction. Such operation is repeated at necessary times, and thereby, plural partial images are acquired over the entire one breast. In the first example, scanning is performed at three times in the X-axis direction, and thus, one ultrasonic slice image is formed by three partial images in the respective slice locations in the X-axis direction.

In the second example shown in FIG. 7, the ultrasonic probe 16 first performs the first scan by transmitting and receiving ultrasonic waves while moving in the positive X-axis direction, then, moves to a predetermined distance in the negative X-axis direction and the positive Y-axis direction, and performs the second scan by transmitting and receiving ultrasonic waves while moving in the negative X-axis direction. Such operation is repeated at necessary times, and thereby, plural partial images are acquired over the entire one breast. In the second example, scanning is performed at three times in the X-axis direction, and thus, one ultrasonic slice image is formed by three partial images in the respective slice locations in the X-axis direction.

In the third example shown in FIG. 8, using an ultrasonic probe 16a having a substantially large size (the length in the Y-axis direction) compared to the size of the breast, scanning is completed by moving the ultrasonic probe 16a once in the positive X-axis direction, and ultrasonic slice images in the respective locations in the X-axis direction are acquired.

In the third example shown in FIG. 8, since the ultrasonic slice images in the respective locations in the X-axis direction are acquired, the B-mode image data generated by the B-mode image data generating unit 46 represents the respective ultrasonic slice images. On the other hand, since the plural partial images are acquired in the first example shown in FIG. 6 or in the second example shown in FIG. 7, it is necessary to correlate the plural partial images in order to obtain one ultrasonic slice image by synthesizing one set of partial images in each slice location in the X-axis direction.

Figure 9:
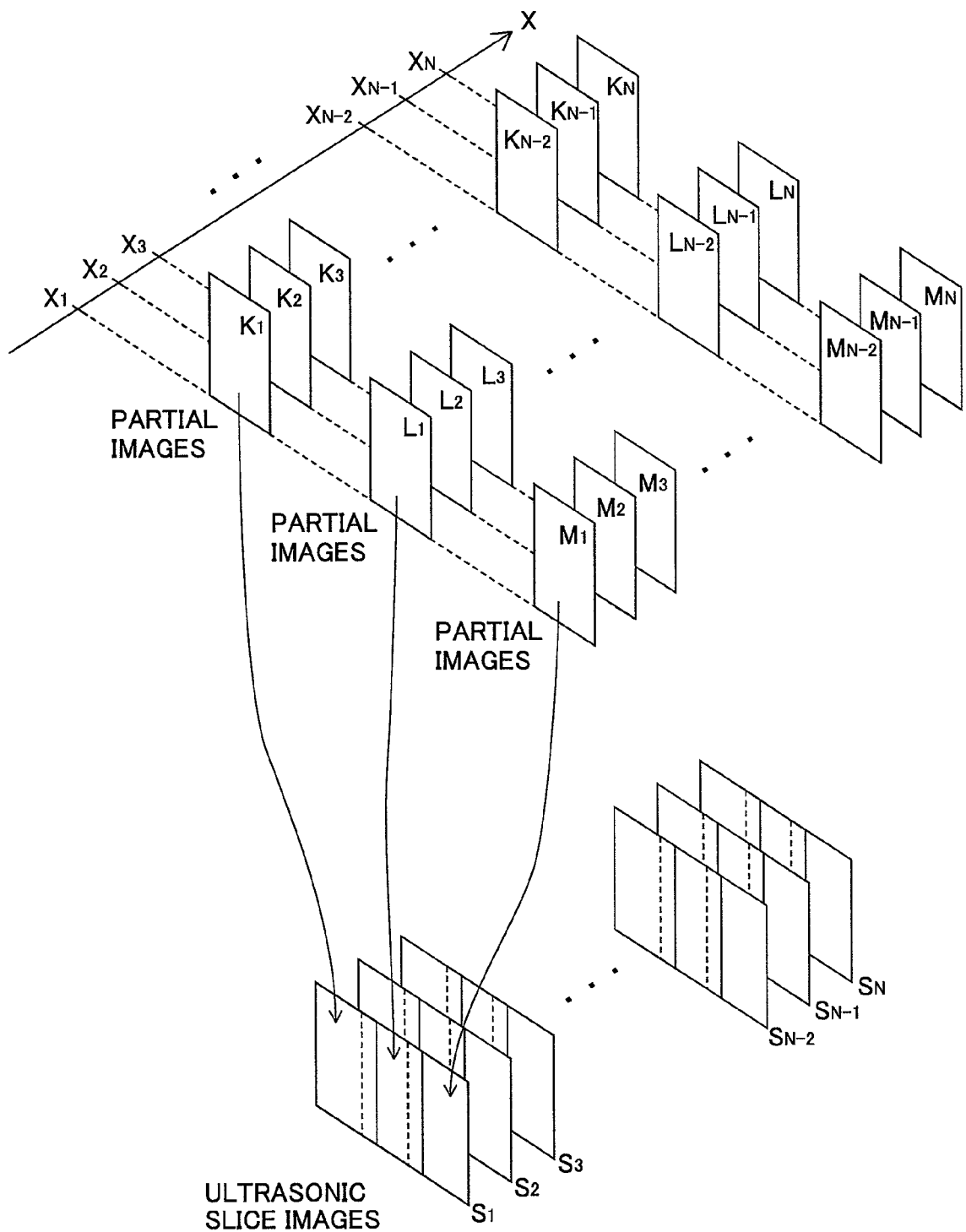
FIG. 9 is a diagram for explanation of correlations between the plural partial images.

FIG. 9 is a diagram for explanation of correlations between the plural partial images. Here, the case where one ultrasonic slice image is formed by three partial images will be explained. As shown in FIG. 9, in slice locations $X_1$, $X_2$, ..., $X_N$ in the X-axis direction, partial images $K_1$, $K_2$, ..., $K_N$ are acquired by the first scan, partial images $L_1$, $L_2$, ..., $L_N$ are acquired by the second scan, and partial images $M_1$, $M_2$, ..., $M_N$ are acquired by the third scan. In this case, ultrasonic slice images $S_1$, $S_2$, ..., $S_N$ are formed by synthesizing three partial images in the respective slice locations in the X-axis direction. For example, ultrasonic image $S_1$ is formed by synthesizing the partial image $K_1$, the partial image $L_1$, and the partial image $M_1$.

For the purpose, the data storage unit 51 of the medical imaging apparatus shown in FIG. 2 stores B-mode image data representing plural partial images and information on correlations between the plural partial images. This information includes X-coordinates and Y-coordinates of the ultrasonic probe 16 outputted from the location movement control unit 20 when ultrasonic imaging is performed, for example. The image processing unit 52 forms one ultrasonic slice image by synthesizing one set of partial images represented by the B-mode image data loaded from the data storage unit 51 based on the information on the correlation loaded from the data storage unit 51.

Alternatively, the image processing unit 52 does not necessarily perform the synthesis of partial images, but the data management unit 142 of the medical image storage apparatus shown in FIG. 4 may store the information on the correlations between plural partial images together with the first and second image data and location data in the storage unit, and the display control unit 153 of the medical image display apparatus shown in FIG. 1 may synthesize one set of partial images represented by the first image data loaded from the medical image storage apparatus 140 to form one ultrasonic slice image based on the information on the correlation loaded from the medical image storage apparatus 140.

Furthermore, the information on the correlations between plural partial images is not necessarily stored, but the display control unit 153 of the medical image storage apparatus may synthesize one set of partial images represented by the first image data loaded from the medical image storage apparatus 140 to form one ultrasonic slice image by determining the correlations between plural partial images represented by the first image data loaded from the medical image storage apparatus 140 based on the location data, the order of those partial images, and/or contents of those partial images and so on loaded from the medical image storage apparatus 140.

The invention claimed is:

1. A medical image diagnostic system comprising:
a medical imaging apparatus configured to acquire a radiation image of an object to be inspected projected on a projection surface by applying radiation to the object, acquiring an ultrasonic slice image of the object along a slice surface substantially orthogonal to said projection surface by transmitting ultrasonic waves toward the object and receiving ultrasonic echoes reflected by the object, and generating first image data representing plural ultrasonic slice images along plural slice surfaces, second image data representing at least one radiation image along a surface substantially orthogonal to the plural slice surfaces, and location data representing locations of said plural slice surfaces on said projection surface;
a medical image storage apparatus configured to correlate and store the first image data, the second image data, and the location data generated by said medical imaging apparatus; and
a medical image display apparatus configured to display at least one ultrasonic slice image along at least one slice surface based on the first image data loaded from said medical image storage apparatus, and to display at least one radiation image along a surface substantially orthogonal to the at least one slice surface and a marker indicating a location of said at least one slice surface on said projection surface based on the second image data and the location data loaded from said medical image storage apparatus.

2. A medical imaging apparatus comprising:
a radiation imaging section configured to acquire a radiation image of an object to be inspected projected on a projection surface by applying radiation to the object;
an ultrasonic imaging section configured to acquire an ultrasonic slice image of the object along a slice surface substantially orthogonal to said projection surface by transmitting ultrasonic waves toward the object and receiving ultrasonic echoes reflected by the object; and
an imaging control section configured to generate first image data representing plural ultrasonic slice images along plural slice surfaces, second image data representing at least one radiation image along a surface substantially orthogonal to the plural slice surfaces, and location data representing locations of said plural slice surfaces on said projection surface by controlling said radiation imaging section and said ultrasonic imaging section.

3. The medical imaging apparatus according to claim 2, wherein said radiation imaging section includes a radiation emitting unit configured to emit radiation, a radiation detection unit for detecting radiation emitted by said radiation emitting unit and passing through the object, an imaging stage provided between said radiation emitting unit and said radiation detection unit, and a compression plate configured to compress the object between said imaging stage and itself, and
said ultrasonic imaging section includes an ultrasonic probe configured to transmit and receive ultrasonic waves while moving along an opposite surface to the compression surface of said compression plate, and acquires the plural ultrasonic slice images of the object along the plural slice surfaces substantially orthogonal to said projection surface.

4. The medical imaging apparatus according to claim 3, wherein one ultrasonic slice image is formed by a predetermined number of partial images of the plural partial images acquired by imaging the object while moving said ultrasonic probe along said compression plate, and said imaging control section synthesizes the predetermined number of partial images of the plural partial images to form one ultrasonic slice image.

5. The medical imaging apparatus according to claim 3, wherein one ultrasonic slice image is formed by a predetermined number of partial images of the plural partial images acquired by imaging the object while moving said ultrasonic probe along said compression plate, and said imaging control section generates information on correlations between the plural partial images together with the first image data representing the plural partial images.

6. The medical imaging apparatus according to claim 2, wherein, regarding symmetric organs of the object, said imaging control section generates first image data representing an ultrasonic slice image of a left organ along a first slice surface and an ultrasonic slice image of a right organ along a second slice surface symmetrically with respect to a central axis which represents respective line segments predetermined for the symmetric organs, and generates second image data representing a radiation image of the left organ and a radiation image of the right organ symmetrically with respect to a central axis which represents respective line segments predetermined for the symmetric organs.

7. A medical image storage apparatus comprising:
an interface unit connected via a network to a medical imaging apparatus configured to acquire a radiation image of an object to be inspected projected on a projection surface by applying radiation to the object, acquiring an ultrasonic slice image of the object along a slice surface substantially orthogonal to said projection surface by transmitting ultrasonic waves toward the object and receiving ultrasonic echoes reflected by the object; and
a data management unit configured to correlate first image data representing plural ultrasonic slice images along plural slice surfaces, second image data representing at least one radiation image along a surface substantially orthogonal to the plural slice surfaces, and location data representing locations of said plural slice surfaces on said projection surface based on the data obtained by said medical imaging apparatus and allowing a storage unit to store the data.

8. The medical image storage apparatus according to claim 7, wherein one ultrasonic slice image is formed by a predetermined number of partial images of the plural partial images acquired by imaging the object while moving an ultrasonic probe along a compression plate, and said data management unit allows said storage unit to store information on correlations between the plural partial images together with the first image data representing the plural partial images.

9. A medical image display apparatus comprising:
an interface unit connected via a network to a medical image storage apparatus configured to correlate and store first image data representing plural ultrasonic slice images along plural slice surfaces, second image data representing at least one radiation image, and location data representing locations of said plural slice surfaces on said projection surface, based on data obtained by a medical imaging apparatus configured to acquire a radiation image of an object to be inspected projected on a projection surface by applying radiation to the object, acquiring an ultrasonic slice image of the object along a slice surface substantially orthogonal to said projection surface by transmitting ultrasonic waves toward the object and receiving ultrasonic echoes reflected by the object;

a first display unit configured to display at least one ultrasonic slice image;

a second display unit configured to display at least one radiation image; and a display control unit configured to allow said first display unit to display at least one ultrasonic slice image along at least one slice surface based on the first image data, and allow said second display unit to display at least one radiation image along a surface substantially orthogonal to the at least one slice surface and a marker indicating a location of said at least one slice surface on said projection surface based on the second image data and the location data.

10. The medical image display apparatus according to claim 9, further comprising:

an operation unit to be operated for changing a location of the marker displayed on said second display unit;

wherein, when the location of the marker is changed, the display control unit allows said first display unit to display at least one ultrasonic slice image along at least one slice surface corresponding to a new location of the marker.

11. The medical image display apparatus according to claim 9, further comprising:

an operation unit to be operated for changing at least one ultrasonic slice image displayed on said first display unit;

wherein, when the at least one ultrasonic slice image displayed on said first display unit is changed, said display control unit changes a location of the marker displayed on said second display unit to indicate a location of a slice surface of new at least one ultrasonic slice image.

12. The medical image display apparatus according to claim 9, wherein, regarding symmetric organs of the object, said display control unit allows said first display unit to display an ultrasonic slice image of a left organ along a first slice surface and an ultrasonic slice image of a right organ along a second slice surface symmetrically with respect to a central axis which represents respective line segments predetermined for the symmetric organs, and allows said second display unit to display a radiation image of the left organ, on which a location of said first slice surface on a first projection surface is indicated, and a radiation image of the right organ, on which a location of said second slice surface on a second projection surface is indicated, symmetrically with respect to a central axis which represents respective line segments predetermined for the symmetric organs.

13. The medical image display apparatus according to claim 9, wherein one ultrasonic slice image is formed by a predetermined number of partial images of the plural partial images acquired by imaging the object while moving an ultrasonic probe along a compression plate, and said medical image storage apparatus stores information on correlations between the plural partial images together with the first image data representing the plural partial images, said display control unit synthesizes the predetermined number of partial images represented by the first image data loaded from said medical image storage apparatus to form one ultrasonic slice image based on the information on correlations between the plural partial images loaded from said medical image storage apparatus.

14. The medical image display apparatus according to claim 9, wherein one ultrasonic slice image is formed by a predetermined number of partial images of the plural partial images acquired by imaging the object while moving an ultrasonic probe along a compression plate, and said display control unit synthesizes the predetermined number of partial images to form one ultrasonic slice image by determining the correlations between the plural partial images represented by the first image data loaded from said medical image storage apparatus based on the location data at least loaded from said medical image storage apparatus.

15. The medical image diagnostic system according to claim 1, wherein:

said medical imaging apparatus generates first image data representing plural ultrasonic slice images along plural slice surfaces substantially orthogonal to said projection surface, second image data representing at least one radiation image along said projection surface, and location data representing locations of said plural slice surfaces on said projection surface; and said medical image display apparatus displays at least one ultrasonic slice image along at least one slice surface substantially orthogonal to said projection surface based on the first image data loaded from said medical image storage apparatus, and displays at least one radiation image along said projection surface and a marker indicating a location of said at least one slice surface on said projection surface based on the second image data and the location data loaded from said medical image storage apparatus.

16. The medical imaging apparatus according to claim 2, wherein:

said imaging control section generates first image data representing plural ultrasonic slice images along plural slice surfaces substantially orthogonal to said projection surface, second image data representing at least one radiation image along said projection surface, and location data representing locations of said plural slice surfaces on said projection surface by controlling said radiation imaging section and said ultrasonic imaging section.

17. The medical image storage apparatus according to claim 7, wherein:

said data management unit correlates first image data representing plural ultrasonic slice images along plural slice surfaces substantially orthogonal to said projection surface, second image data representing at least one radiation image along said projection surface, and location data representing locations of said plural slice surfaces on said projection surface based on the data obtained by said medical imaging apparatus, and allows a storage unit to store the data.

18. The medical image display apparatus according to claim 9, wherein:

said display control unit allows said first display unit to display at least one ultrasonic slice image along at least one slice surface substantially orthogonal to said projection surface based on the first image data, and allows said second display unit to display at least one radiation image along said projection surface and a marker indicating a location of said at least one slice surface on said projection surface based on the second image data and the location data.

* * * * *